(12) United States Patent
Sinn et al.

(10) Patent No.: US 6,410,695 B1
(45) Date of Patent: Jun. 25, 2002

(54) INDIVIDUAL MEDICAMENT DOSING CONJUGATE

(75) Inventors: Hannsjörg Sinn, Wiesloch; Wolfgang Maier-Borst, Dossenheim; Hans-Hermann Schrenk, Zeiskam; Gerd Stehle, Heidelberg, all of (DE)

(73) Assignee: Deutsches Krebsforschungszentrum Stiftung Des Öffentlichen Rechts, Heidelberg (DE)

( * ) Notice: Subject to any disclaimer, the term of this patent is extended or adjusted under 35 U.S.C. 154(b) by 0 days.

(21) Appl. No.: 08/913,217

(22) PCT Filed: Feb. 21, 1996

(86) PCT No.: PCT/DE96/00267

§ 371 (c)(1),
(2), (4) Date: Feb. 9, 1998

(87) PCT Pub. No.: WO96/25956

PCT Pub. Date: Aug. 29, 1996

(30) Foreign Application Priority Data

Feb. 21, 1995 (DE) .......................... 195 05 960

(51) Int. Cl.[7] .......................... C07K 1/00; A61K 47/48; A61K 49/02
(52) U.S. Cl. ...................... 530/402; 530/362; 424/1.11; 424/193.1; 514/2; 514/21; 552/200; 552/227
(58) Field of Search ................ 530/362, 402; 424/1.11, 193.1; 552/227, 200; 514/2, 21

(56) References Cited

U.S. PATENT DOCUMENTS 4,118,468 A  10/1978  Strecker et al. ................ 424/1
4,339,426 A  7/1982  Meares et al. ................ 424/1

FOREIGN PATENT DOCUMENTS

| EP | 0 217 577 A2 | 4/1987 |
| EP | 0 243 929 A2 | 11/1987 |
| WO | WO 89/00062 | 1/1989 |
| WO | WO 89/05853 | 6/1989 |
| WO | WO 91/01144 | 2/1991 |
| WO | WO 91/14459 | 10/1991 |
| WO | WO 93/02105 | 2/1993 |
| WO | WO 93/02192 | 2/1993 |
| WO | WO 93/18160 | 9/1993 |
| WO | WO 94/08624 | 4/1994 |
| WO | WO 95/19791 | 7/1995 |
| WO | WO 95/29707 | 11/1995 |
| WO | WO 96/10422 | 4/1996 |

OTHER PUBLICATIONS

Kato, et al., Chemical Abstracts, 121(4): Abstract No. 42716, (1994).

Sinn, et al., "Design of Compounds Having an Enhanced Tumour Uptake, using Serum Albumin as a Carrier. Part 1", *Nucl. Med. Biiol.*—17(8):819–827 (1990).

Nakajima, et al., "In–Labeled Mn–Metalloporphyrin for Tumor Imaging," *Nuel. Med. Biol.* —20(2):231–237 (1993).

Sinn, et al., "Radioactive Labeled Photsensitizers for Tumor Diagnostic and Photodynamic Therapy (PDT)", *J. Labelled Comp. Radiopharm*—(1993).

*Primary Examiner*—Avis M. Davenport
(74) *Attorney, Agent, or Firm*—Albert P. Halluin; Viola T. Kung; Howrey Simon Arnold & White, LLP

(57) ABSTRACT

The present invention relates to a conjugate comprising an active substance and a compound having a binding site for metallic compounds. In addition, this invention relates to a process for the preparation of such a conjugate and its use.

9 Claims, 19 Drawing Sheets

(SE= Succinimidylester)

Alizarin-HSA

+ Me²⁺ (Cu, Co, Ni, Zn )

Alizarin-7-Chlortetracycline Complex

7- Chlortetracycline-Alizarin-HSA

Triethylenetetraamine-hexaacetic acid-amino-PEG 3

INDIVIDUAL MEDICAMENT DOSING CONJUGATE

The present application is a U.S. nationalization pursuant to 35 U.S.C. 371 of PCT/DE96/00267 filed on Feb. 21, 1996 which is in turn based on German Patent Application No. 195 05 960.3 filed on Feb. 21, 1995.

FIELD OF THE INVENTION

The present invention relates to a conjugate for individually dosing pharmaceutical preparations, a process for the production of such a conjugate as well as its use.

BACKGROUND OF THE INVENTION

For a long time there has been a great demand to individually dose pharmaceutical preparations, i.e., accurately adapt their dose to a patient's therapy course. This need is given particularly when chemotherapeutic agents are used. Many attempts have been made to achieve the above. However, the attempts have only showed little success by now.

BRIEF DESCRIPTION OF THE INVENTION

Therefore, it is an object of the present invention to provide for individually dosing pharmaceutical preparations. According to the invention this is achieved by a conjugate which comprises an active substance and a compound having a binding site for metallic compounds.

The expression "active substance" comprises substances of any kind which can be used for treating and/or diagnosing a disease, particularly a tumor, an infectious disease, skin disease and a disease of the immune system.

Examples of such substances include chemotherapeutic agents, e.g., antibiotics, virostatics, antiprotozoals and cytostatic agents. Examples of antibiotics include sulfonamides, tetracyclines, e.g., 7-chlorotetracycline, fusidic acid, gyrase inhibitors, e.g., quinolones, amphotericin, isoniazid, pyrazine 2-carboxylic acid, and pyrazinamide. Examples of virostatics include amantadine and rimantadine. Examples of antiprotozoals are mefloquine and primaquine. Examples of cytostatic agents are anthracyclines, e.g., doxorubicin, topoisomerase inhibitors, mitomycin A and C, bleomycinic acid, chlorambucil, melphalan and antifolates e.g., methotrexate. Furthermore such a substance may be an aminoanthraquinone such as celliton blue and acid black. Moreover, such a substance may be a photoactive substance, e.g., a porphyrin such as o-, m- and/or p-tetrahydroxyphenylporphine, o, m- and/or p-tetracarboxyphenylporphine and o-, m- and/or p-tetrasulfophenylporphine, a chlorin such as o-, m- and/or p-tetrabydroxyphenylchlorin, o-, m- and/or tetracarboxyphenylchlorin and o-, m- and/or p-tetrasulfophenylchlorin, or a bacteriochlorin, o-, m- and/or p-tetrahydroxyphenylbacteriochlorin such as o-, m- and/or p-tetracarboxyphenylbacteriochlorin, and o-, m- and/or p-tetrasulfophenylbacteriochlorin. In addition, such a substance may be a contrast medium for fluorospectroscopy, e.g., trifluoroacetic acid, nuclear resonance scanning or scintiscanning.

One or more of the above substances and/or analogues or derivatives thereof are present in a conjugate according to the invention. If several are present, they may be the same or differ from one another.

The expression "compound having a binding site for metallic compounds" includes compounds of any kind which have binding sites for metallic compounds. Examples of such binding sites include hydroxyl groups, particularly C-atoms bound hydroxyl groups, carbonyl and carboxyl groups. The compound may have one or more binding sites. The compound has preferably 2, more preferably 3 to 6, binding sites. If several binding sites are present, they may be the same or differ from one another. Examples of the above compounds are ethylenediaminetetraacetate (EDTA), diethylenetri-aminepentaacetate (DTPA), triethylenetetra-minehexaacetate (TTHE), alizarin and derivatives thereof.

One or more of the above compounds are present in a conjugate according to the invention. If several are present, they may be the same or differ from one another. The presence of several of the above compounds supports the water solubility of the conjugate and its ability to bind metallic compounds.

DETAILED DESCRIPTION OF THE INVENTION

Figure 1:
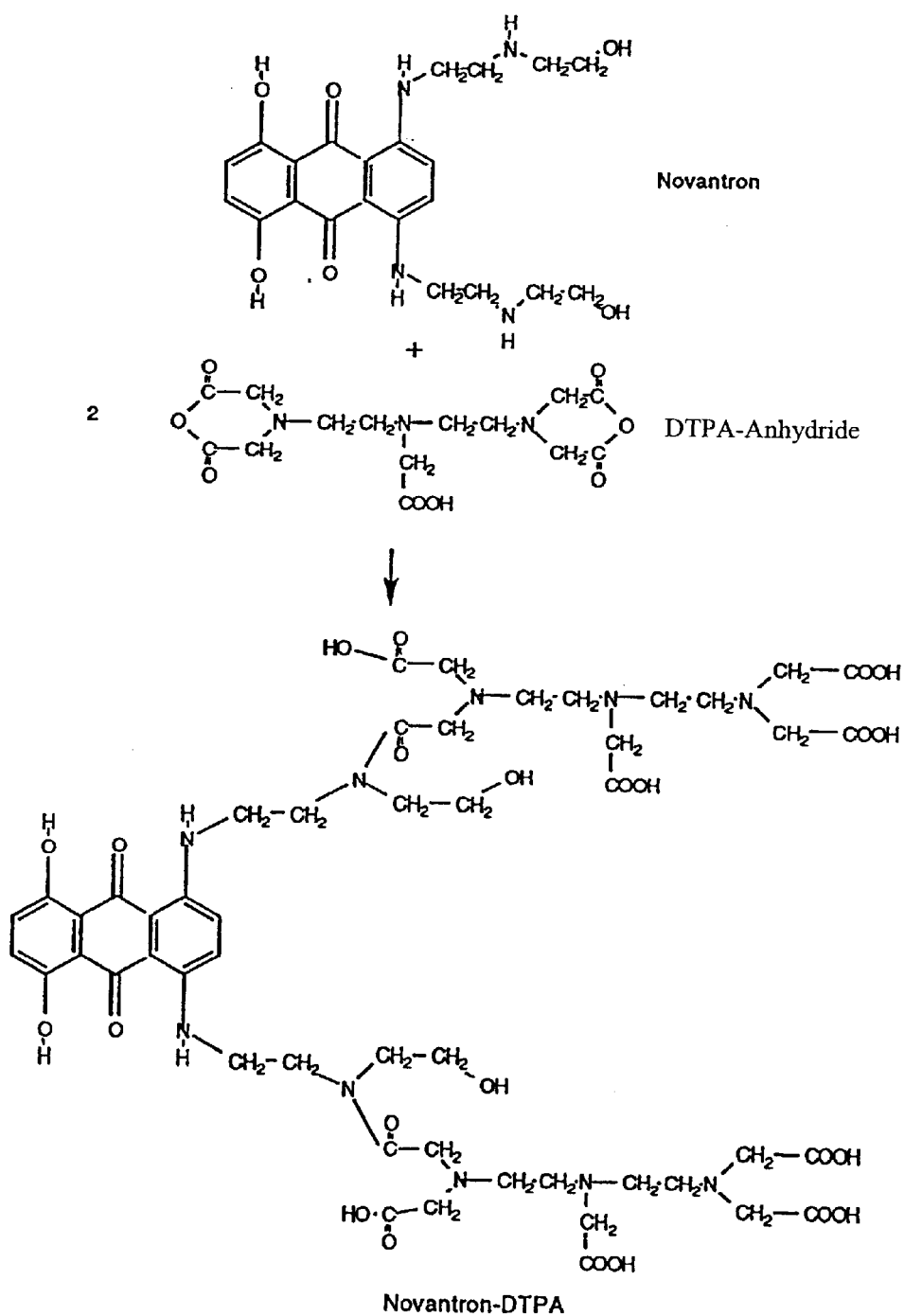
FIG. 1 shows the preparation of the novantron-DTPA-HSA conjugate.
Figure 1:
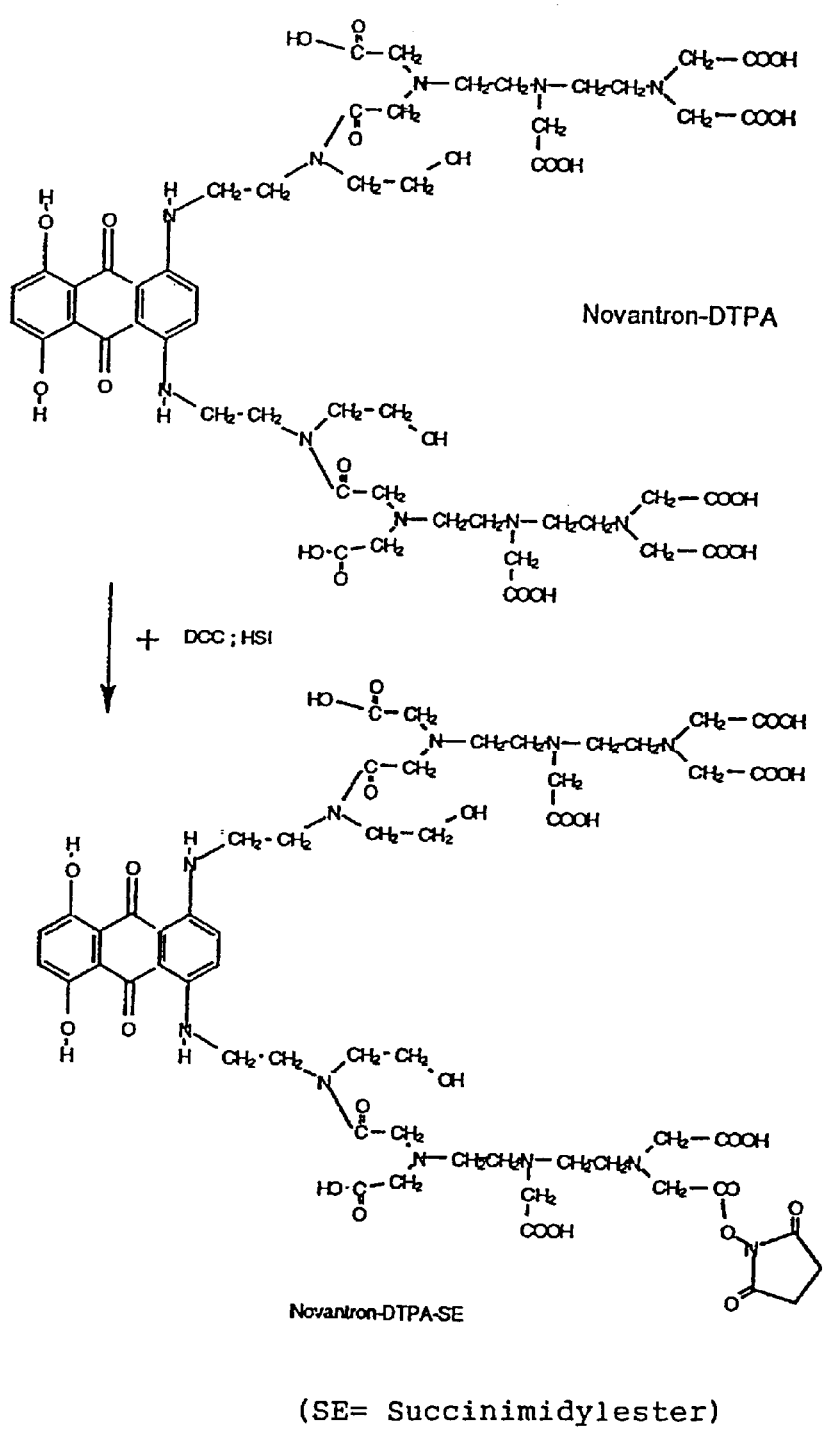
Figure 1:
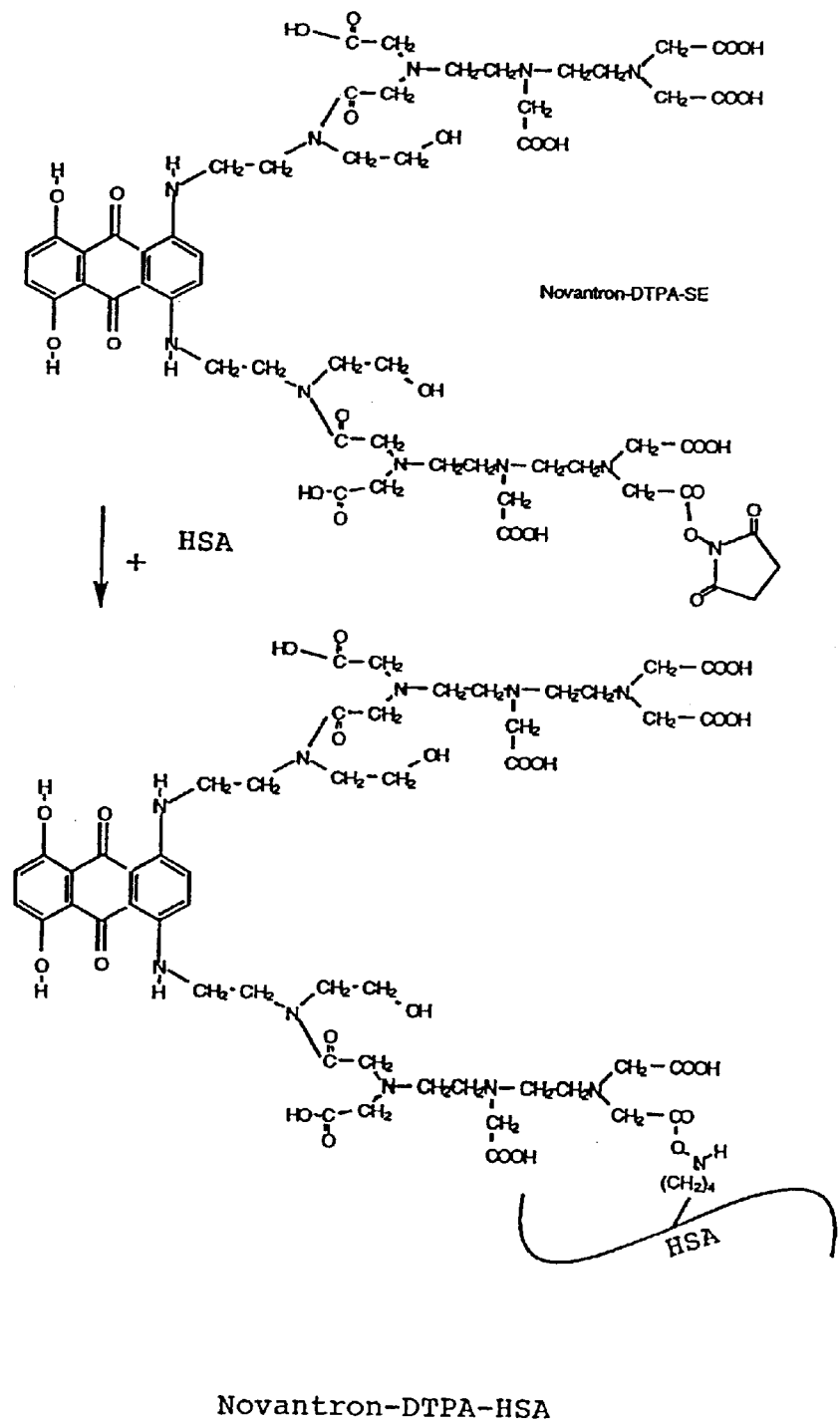

In a preferred embodiment, a conjugate according to the invention has a detectable metallic compound. Such a compound may contain or consist of one or more detectable metals and/or metal ions. Examples of such metals are Zn, Cu, Co, Fe, Ni, Pt, Gd and In, which are preferably bivalent or trivalent, $d^3+$ being especially preferred. The metals and/or metal ions may be radioactive such as 111In.

In another preferred embodiment, a conjugate according to the invention has a carrier. The expression "carrier" comprises compounds of any kind which are suitable to concentrate the conjugate in a certain tissue, e.g., a tumor or a focus of inflammation.

Examples of such carriers include proteins which are not considered exogenous and polyethers. The former are preferably available in native form. In addition, they preferably have a molecular weight of up to 90,000 daltons. Especially preferred is the protein albumin, particularly human serum albumin (HSA), or transferrin. Examples of polyethers are polyethylene glycols such as methoxypolyethylene glycol, methoxypolyethylene glycol-p-nitrophenylcarbonate, methoxypolyethylene glycol succinimidylsuccinate, methoxypolyethylene glycol tresylate, methoxypolyoxyethyleneamine, methoxypolyoxyethylenecarboxylic acid and methoxypolyoxyethyleneimidazolcarbonyl. The polyethers preferably have a molecular weight of 100 to 20,000 daltons, especially preferably about 5,000 daltons.

A conjugate according to the invention may have one or more of the above carriers. If several carriers are present, they may be the same or differ from one another.

In a conjugate according to the invention, one or more active substances may be linked with one or more compounds which have binding sites for metallic compounds. In addition, the active substances and/or the compounds may be linked among one another.

Such a conjugate may also contain one or more detectable metallic compounds. They may be exempt from the linkage between the active substance or active substances and the compound or compounds or represent the same.

An above conjugate may also contain one or more carriers. They may be linked with the active substance or active substances, the compound or compounds and/or the metallic compound or metallic compounds.

The above components of the conjugate according to the invention are given as educts. In the conjugate, they are present in derivatized form. Preferred conjugates according to the invention are illustrated in FIGS. 1 to 6.

A process for the preparation of a conjugate according to the present invention is also provided. Such a process carries out common reactions occurring in chemistry such as activation of an acid group and linkage of the activated acid group with an amino group. In this connection, reference is made to the preparation of the conjugates in Examples 1 and 2 as well as FIGS. 1 to 6.

Conjugates according to the invention may be provided in labeled and unlabeled form. Both forms are well suited for therapeutic purposes. It is favorable to administer the labeled formed al differing times of the treatment so as to determine the absorption and distribution of the conjugate according to the invention in the body and its effect. This renders it possible to dose the conjugate individually. This represents a major advantage that has an effect especially on chemotherapy. The side effects on healthy tissue can be minimized by individually dosing the conjugate. Above all, this is achieved when the conjugate according to the invention contains a carrier that effects a concentration of the conjugate in certain tissues, e.g., tumors or foci of inflammation. Thus, the present invention enables the target-specific and dose-specific administration of pharmaceutical preparations.

EXAMPLES OF THE PREFERRED EMBODIMENTS

The following examples explain the invention.

Example 1

Preparation of the Novantron-DTPA-HSA Conjugate According to the Invention

The preparation of the conjugate and its structure are shown in FIG. 1.

Mitoxantrone (Nevantrone, Lederle Arzncimittel GmbH, Germany) was dissolved in a concentration of 10 mg/ml in 0.17 M Bic. DTPA-anLydride was added in portions to this solution until no more free novantron was detectable under standard conditions by means of thin-layer chromatography.

| TLC: normal conditions | | |
|---|---|---|
| plates: | silica gel 60 (5 × 20 cm) without fluorescence indicator | |
| eluent: | Etac. 70; MeOH 30 (v/v) | |
| Rf. | novantron | 0.53–0.62 |
| | novantron-DTPA | 0.0 |

Then, 2 N HCl was added to the solution until a blue precipitate formed (at about pH 2). The resulting; mixture was subsequently concentrated to dryness in the rotary evaporator.

The residue obtained after the concentration in the rotary evaporator was dissolved in DMF and admixed with two times the molar excess of dicyclohexylcarbodiimide (DCC) and ten times an excess of N-hydroxysuccinimide (HSI). HSA (10 mg/ml in 0.17 M NaHCO$_3$) was added after about 12 hours. The reaction mixture was allowed to stand for about 30 minutes. Thereafter, DCC, DCHH, DMF and HSI were separated as usual. The purity was checked by means of HPLC and TLC. Novantron DTPA-HSA was obtained.

Example 2

Preparation of the Celliton Blue-DTPA-HSA Conjugate According to the Invention

Figure 2:
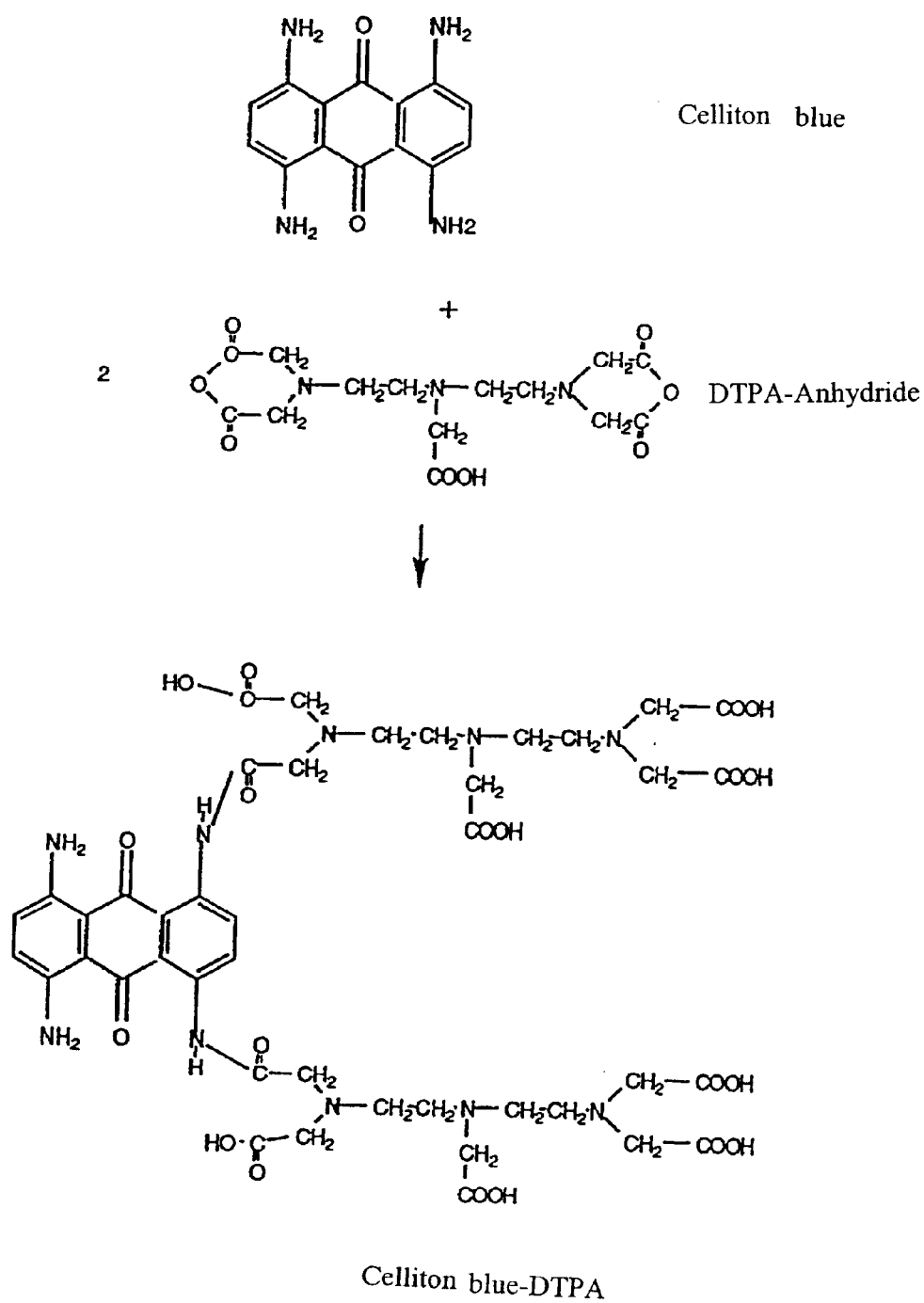
FIG. 2 shows the preparation of the celliton blue-DTPA-HSA conjugate.
Figure 2:
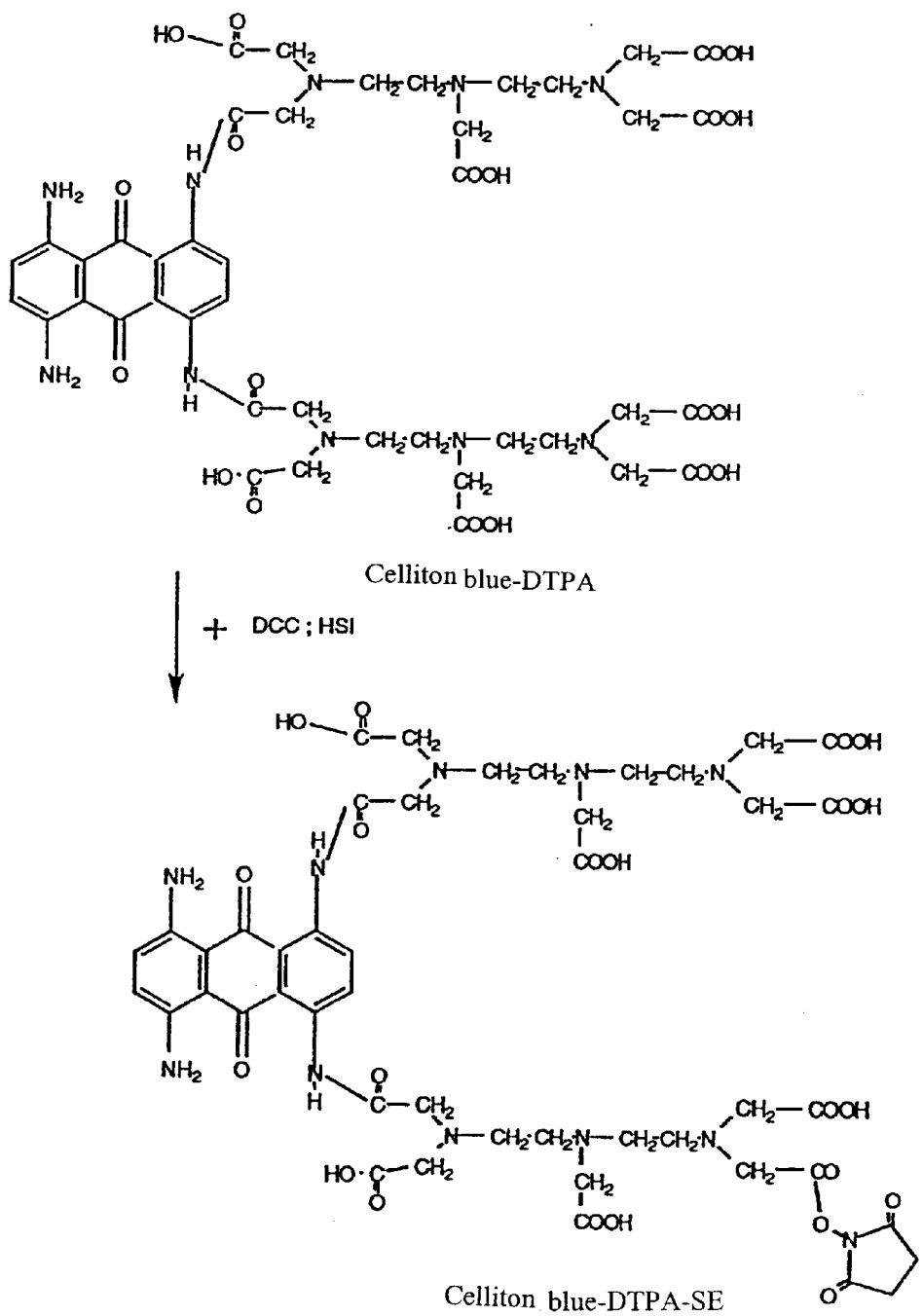
Figure 2:
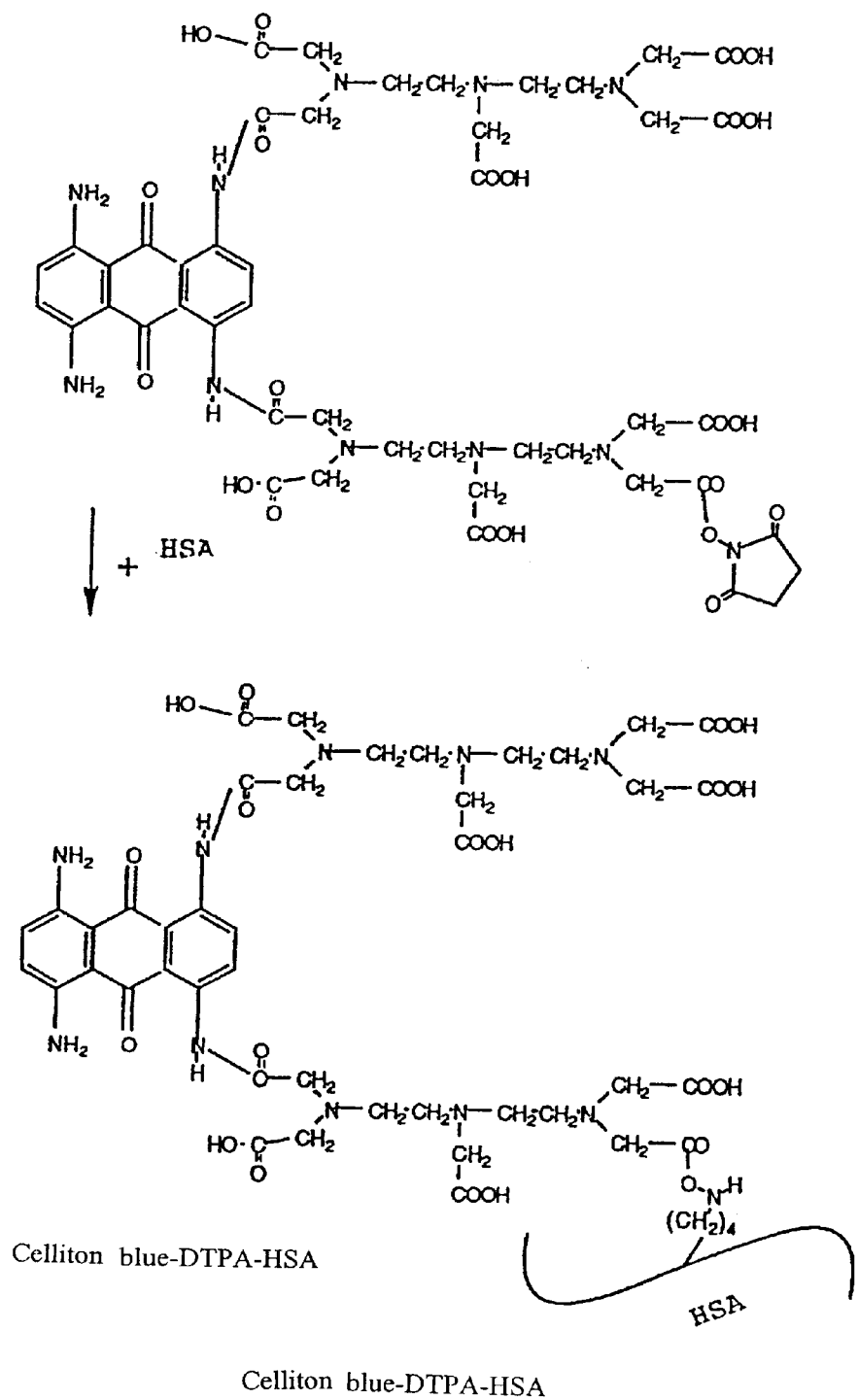
Figure 3:
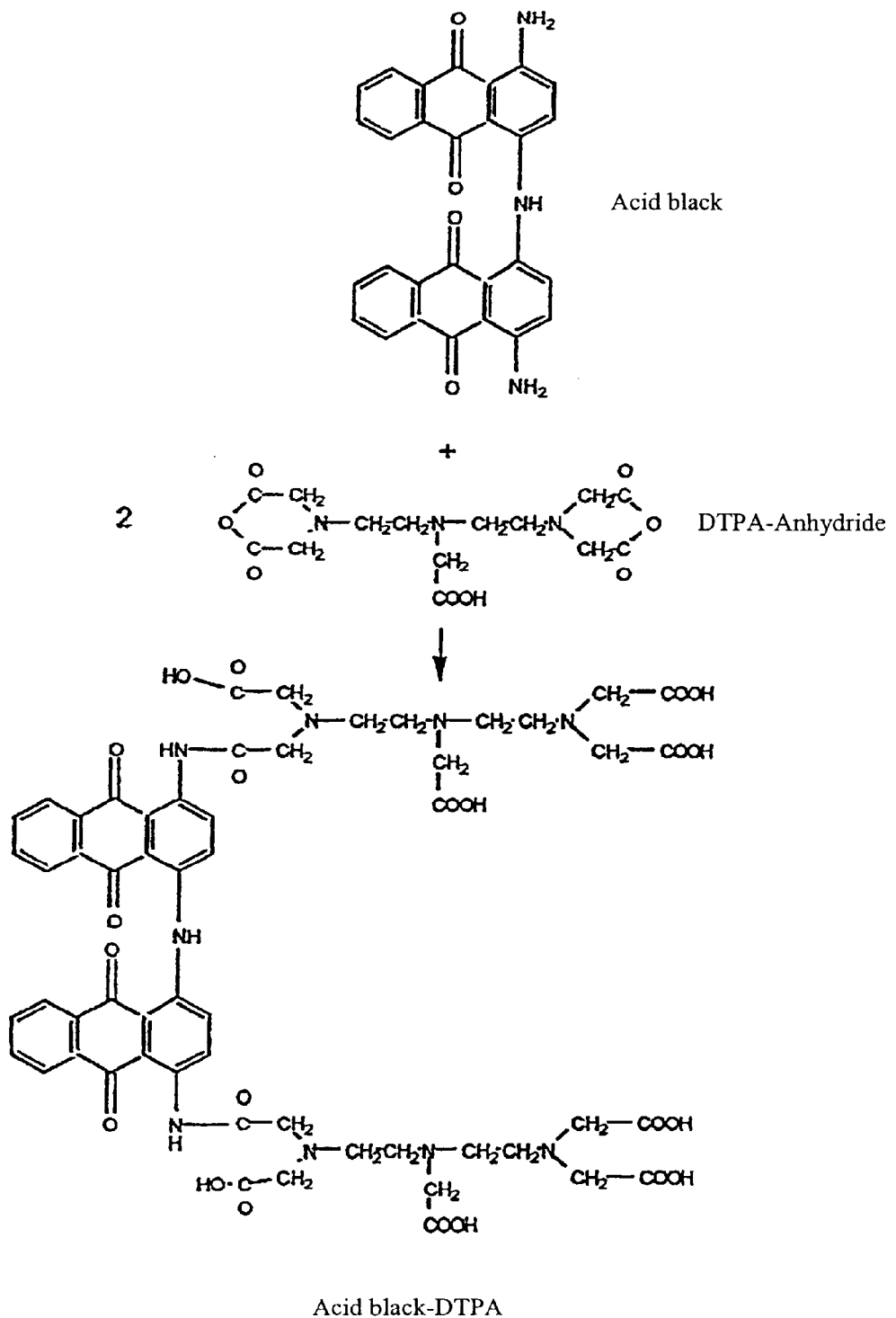
FIG. 3 shows the preparation of the acid black-DTPA conjugate.
Figure 3:
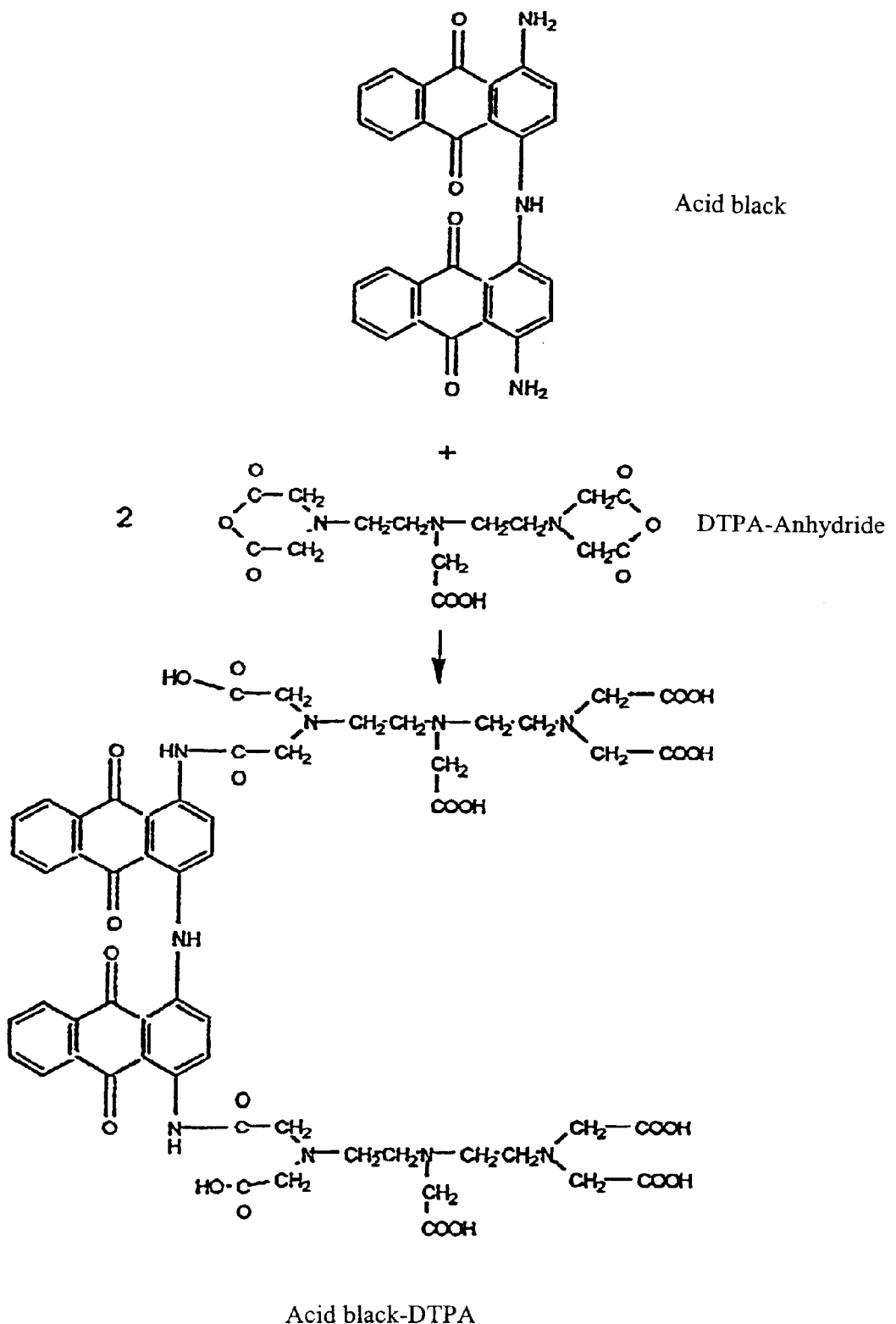
Figure 4:
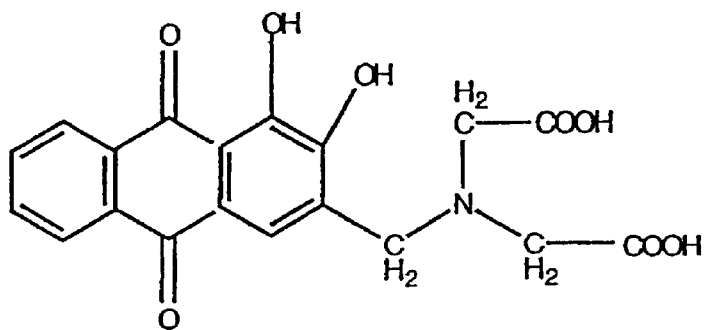
FIG. 4 shows the preparation of the 7-chlorotetracycline-alizarin-HSA conjugate
Figure 4:
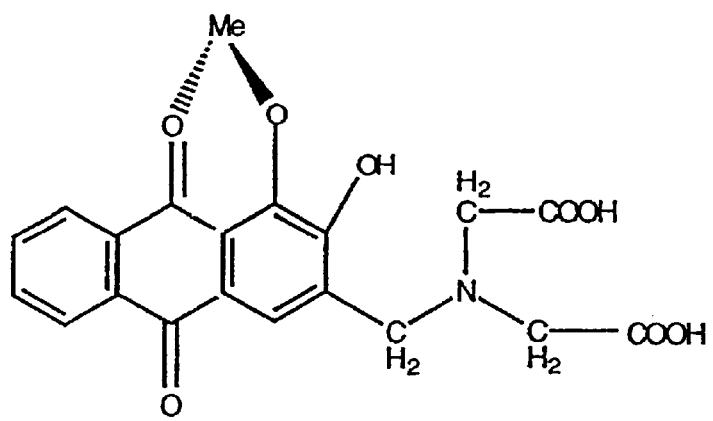
Figure 4:
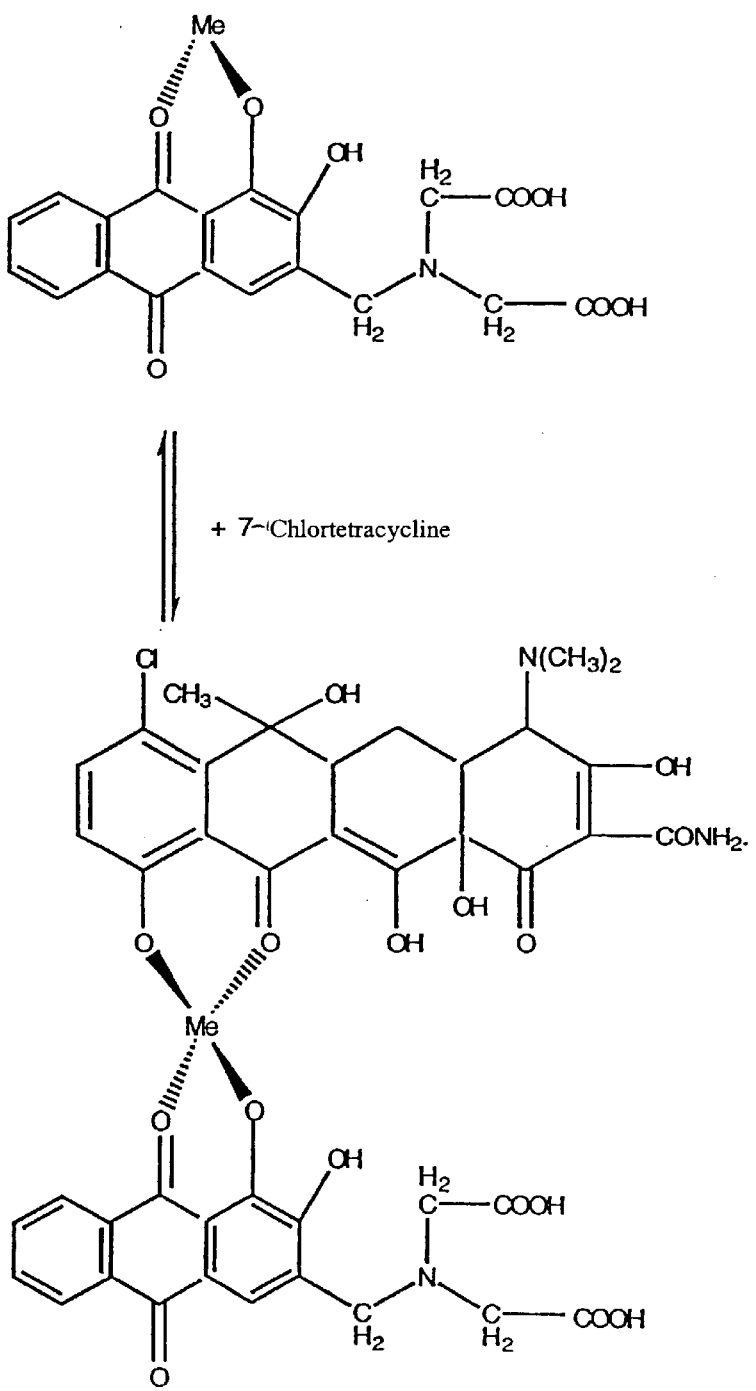
Figure 4:
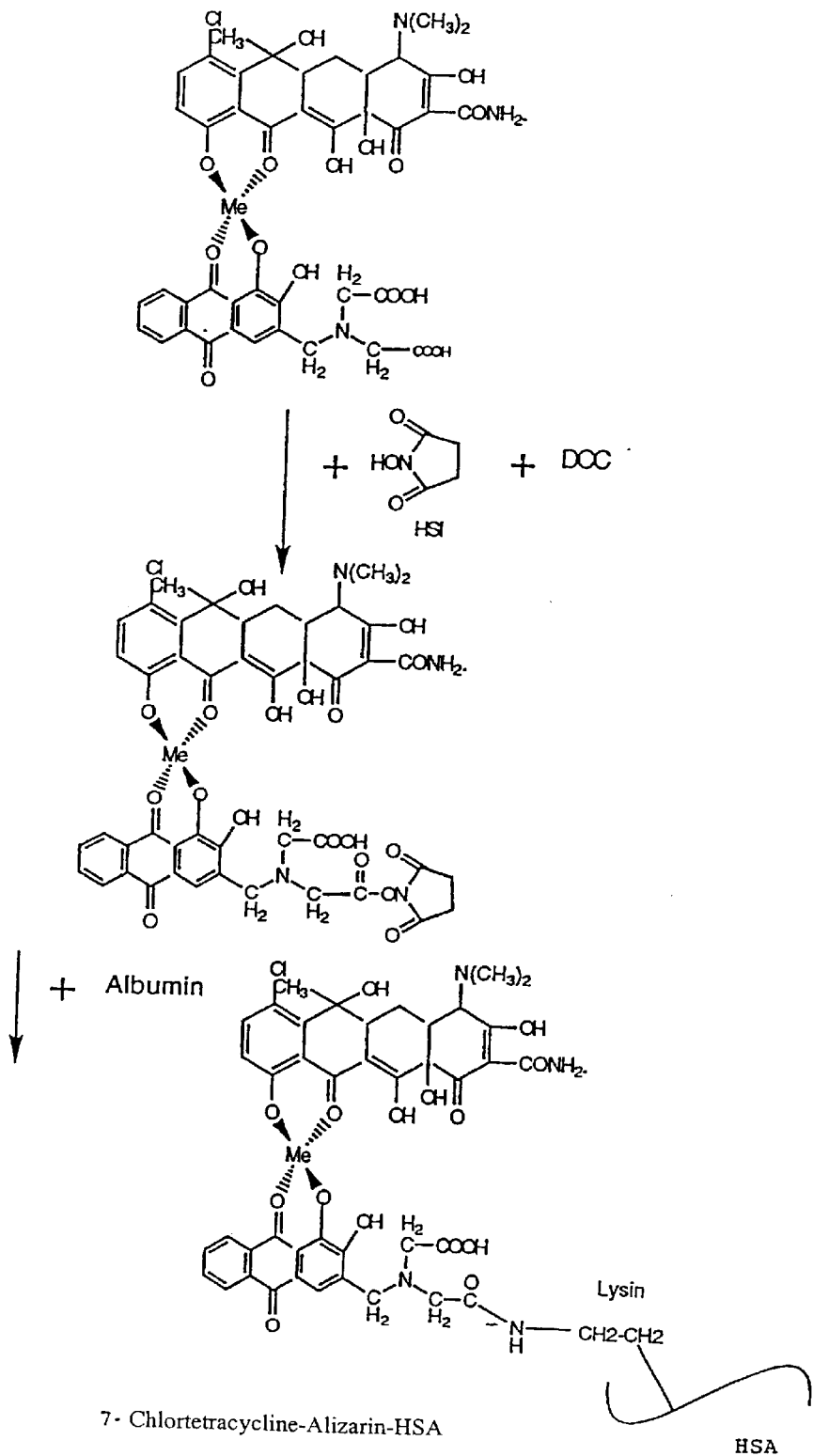
Figure 5:
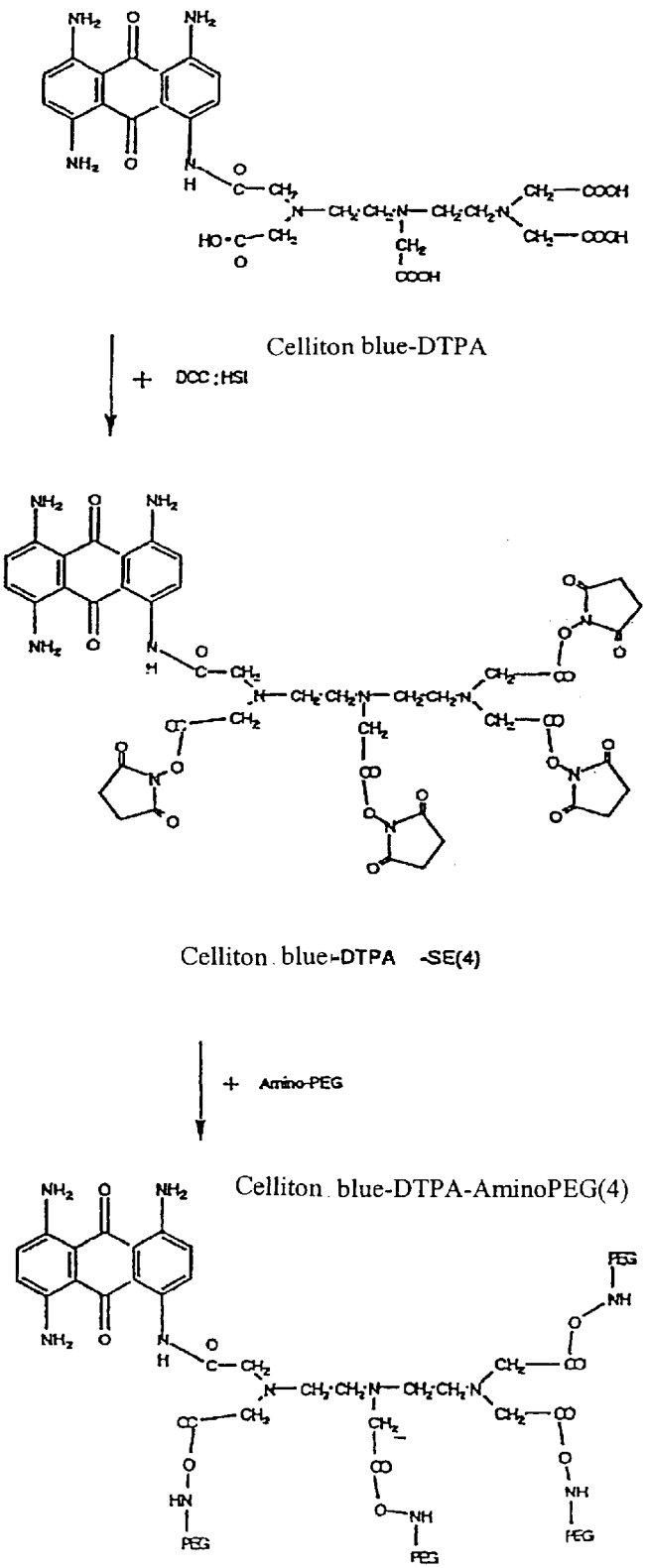
FIG. 5 shows the preparation of the celliton blue-DTPA-PEG conjugate.
Figure 6:
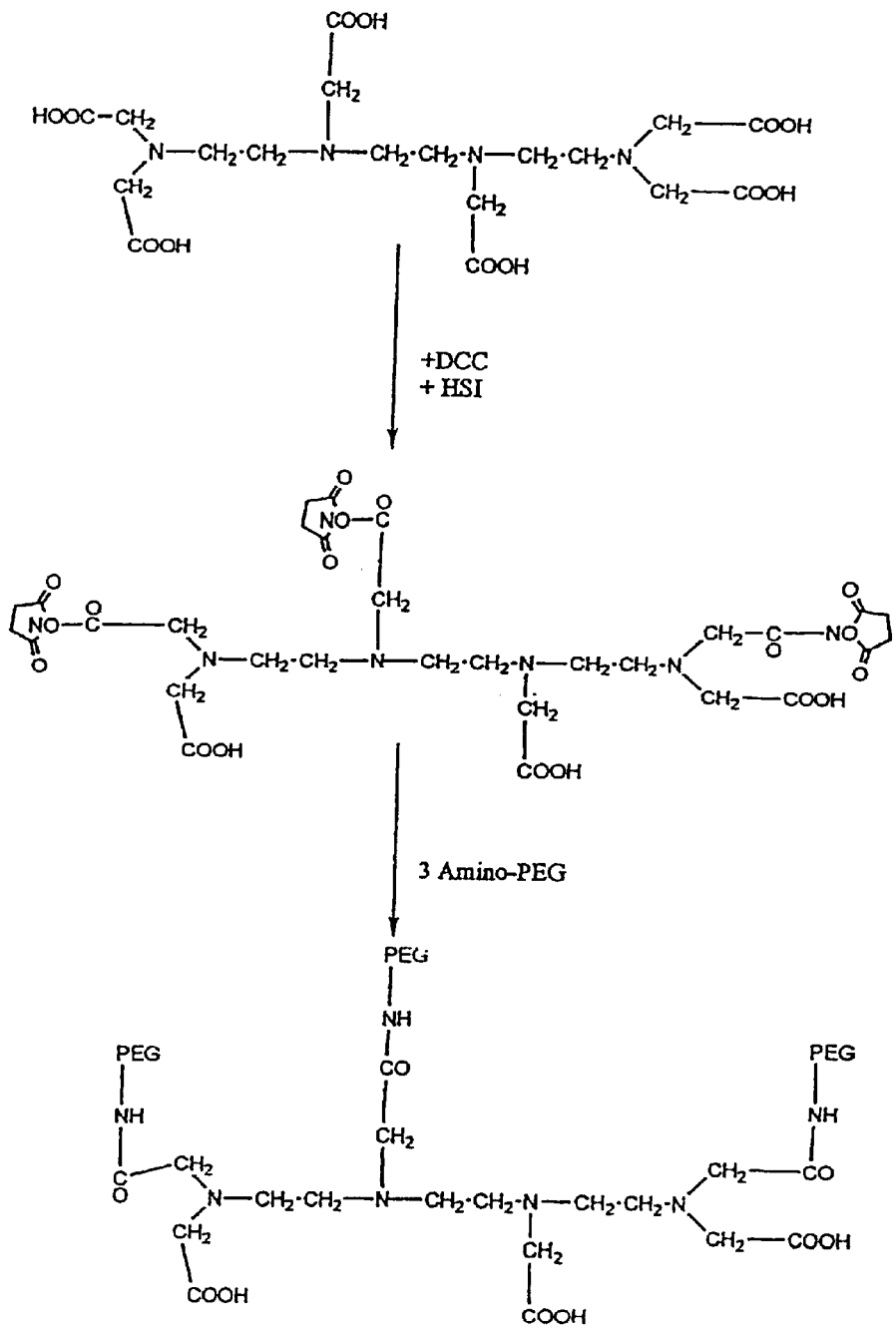
FIG. 6 shows the preparation of the TTHE-PEG(3)-diethylenetramine(3)-DTPA/$Gd^{3+}$ conjugate, the numerals in parentheses indicating the number of the particular compounds in the conjugate.
Figure 6:
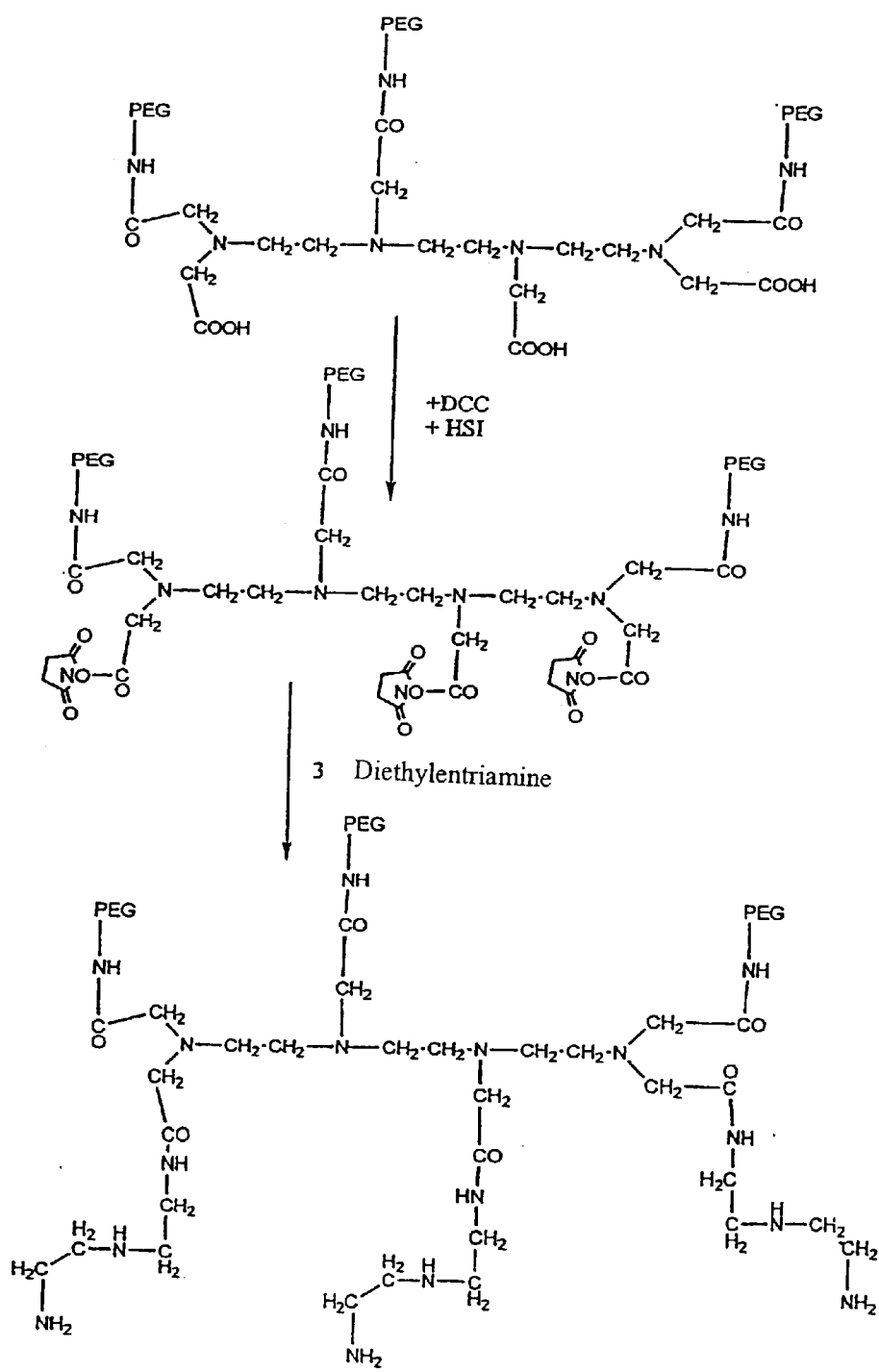
Figure 6:
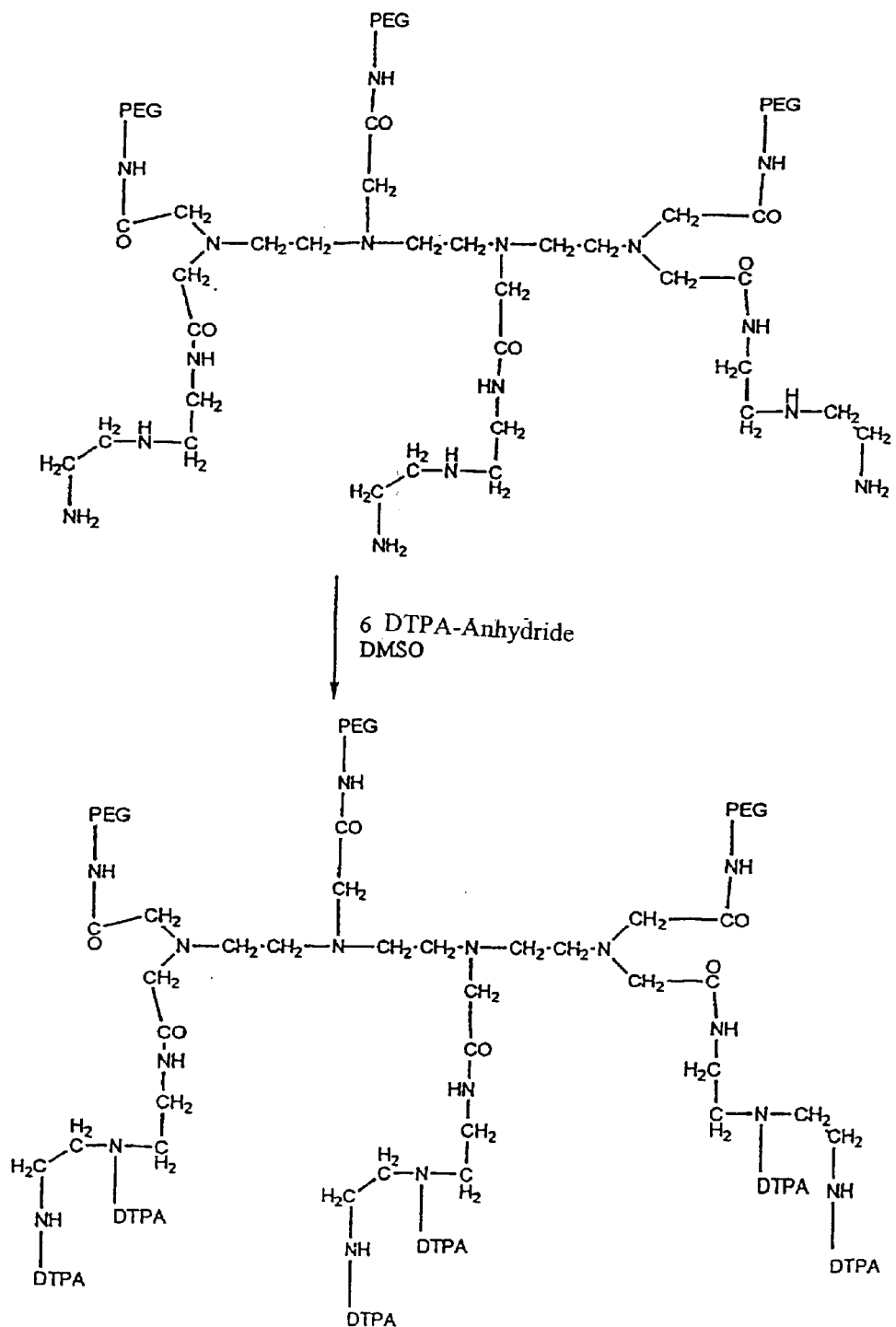
Figure 6:
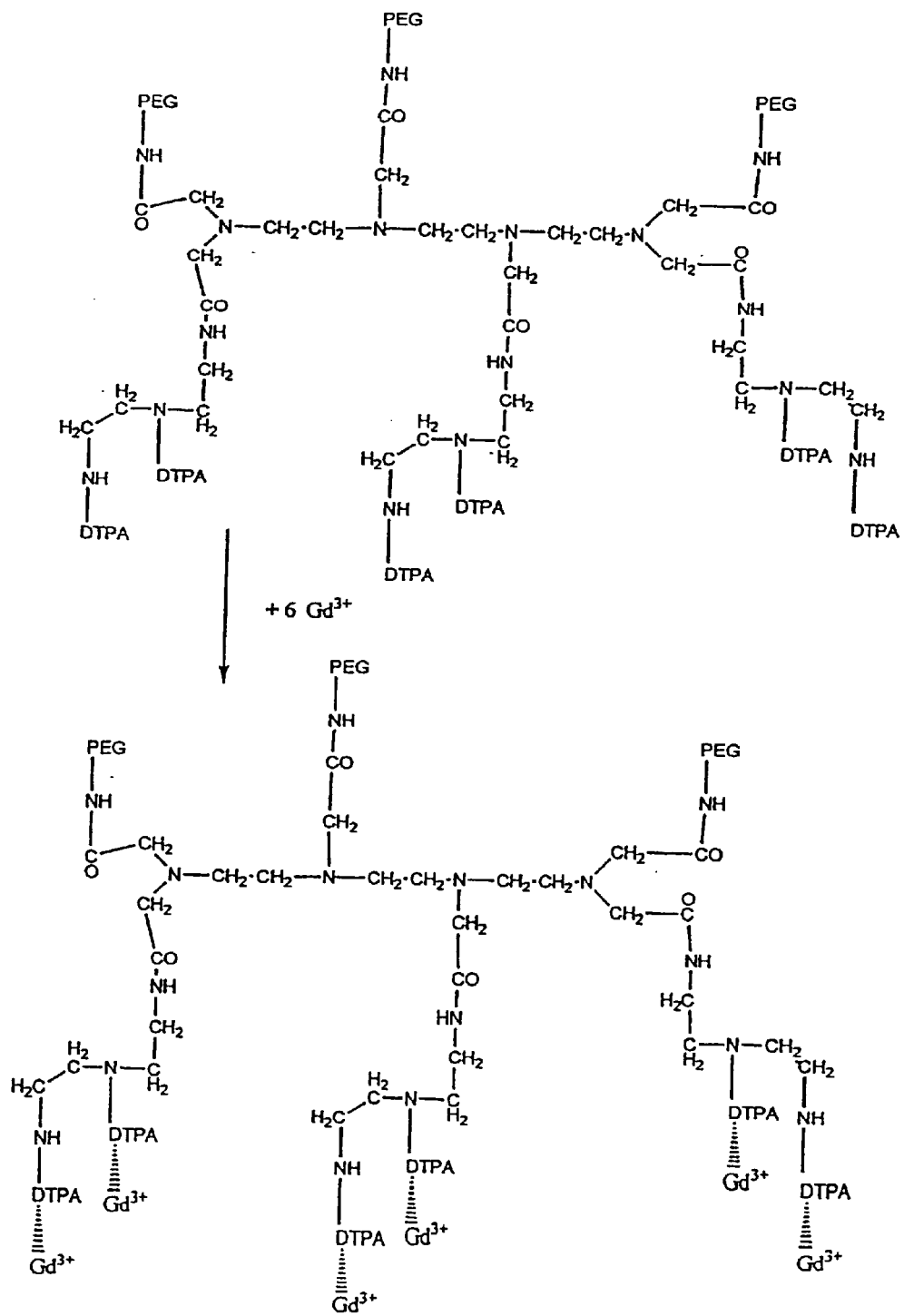

The preparation of the conjugate and its structure are shown in FIG. 2.

Celliton blue (1,4,5,8-tetraaminoantraquinone, MW 268.28) was dissolved in DMF in a concentration of 20 mg/ml. DTPA anhydride was added by stirring until no more free celliton blue was detectable by means of thin-layer chromatography.

| TLC: normal conditions | | |
|---|---|---|
| Rf values: | celliton blue | 0.62–0.66 |
| | celliton blue-DTPA | 0.0 |

The substance dyed bluish violet was purified via ultrafiltration (YC 05), the pH of the solution being adjusted to about 6.5. Then, the solution was acidified using 2 N HCl (pH 2.0–2.5) end directly afterwards concentrated to dryness in the rotary evaporator. The sample was subsequently redissolved in methanol and again concentrated in the rotary evaporator to remove residual water amounts. This was carried out at least three times. Celliton blue-DTPA was reacted with DCC and HSI as described in Example 1. The reaction with HSA took place after 12 to 14 hours. After a reaction period of about 30 minutes, accompanying substances as described in Example 1 were separated. The purity was checked by means of TLC and HPLC. Celliton blue-DTPA-HSA was obtained.

Example 3

Growth Inhibition of Tumor cells by Administration of Celliton Blue-DTPA-HSA and Novantron-DTPA-HSA, Respectively Each of the conjugates celliton blue-DTPA-HSA and novantron-DTPA-HSA as well as HSA as control were incubated with Walker 256 tumor cells under conventional conditions. The cell number per ml was determined as usual after 24 hours and 48 hours, respectively.

Figure 7:
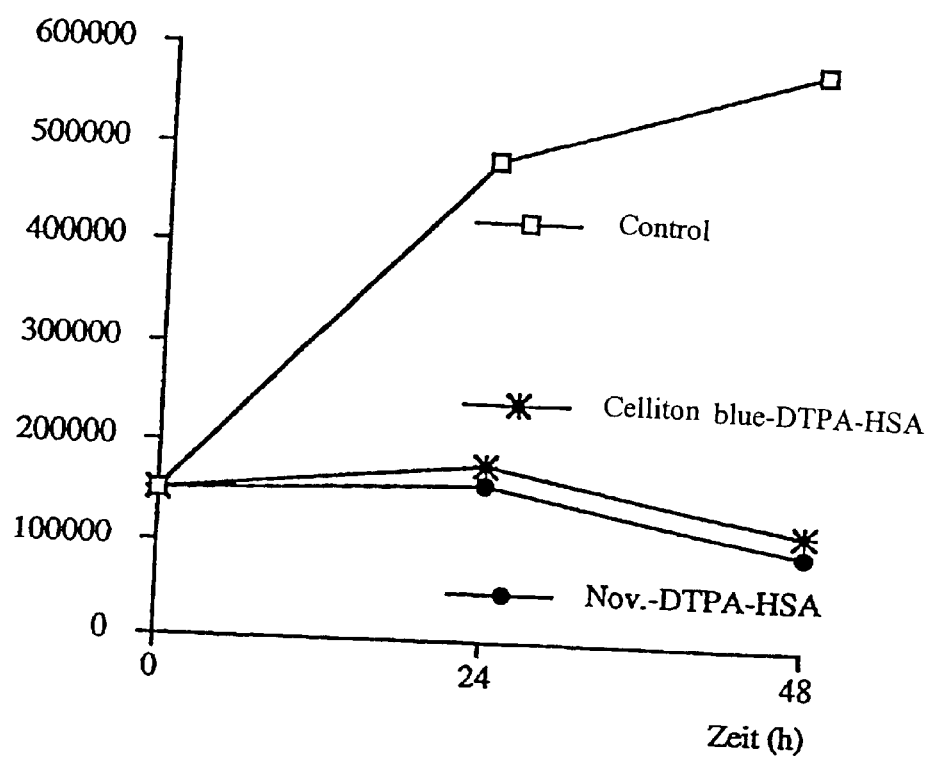
FIG. 7 shows the growth inhibition of tumor cells by administration of celliton blue-DTPA-HSA and novantron-DTPA-HSA, respectively.

FIG. 7 shows that each of the conjugates according to the invention inhibits the proliferation of tumor cells.

Example 4

Growth Inhibition of Tumor Cells by Administration of Acid Black-DTPA

Example 4 was carried out like Example 3, acid black-DTPA being administered as a conjugate.

Figure 8:
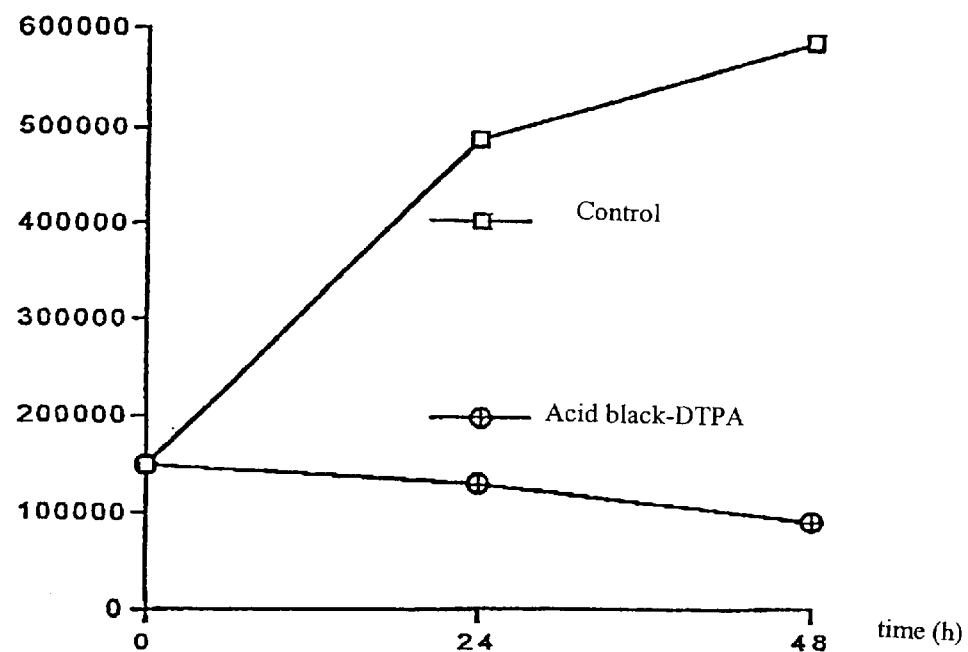
FIG. 8 shows the growth inhibition of tumor cells by administration of acid black-DTPA.

FIG. 8 shows that the conjugate according to the invention inhibits the proliferation of tumor cells.

Example 5

Distribution of 111In-novantron-DTPA-HSA Over the Tumor, Cardiac and Liver Regions A tumor-bearing rat (Walker 256 carcinosarcoma) was given the conjugate according to the invention by intravenous injection. The percentage absorption, based on the total amount of administered conjugate, was measured by means of scintiscanning.

Figure 9:
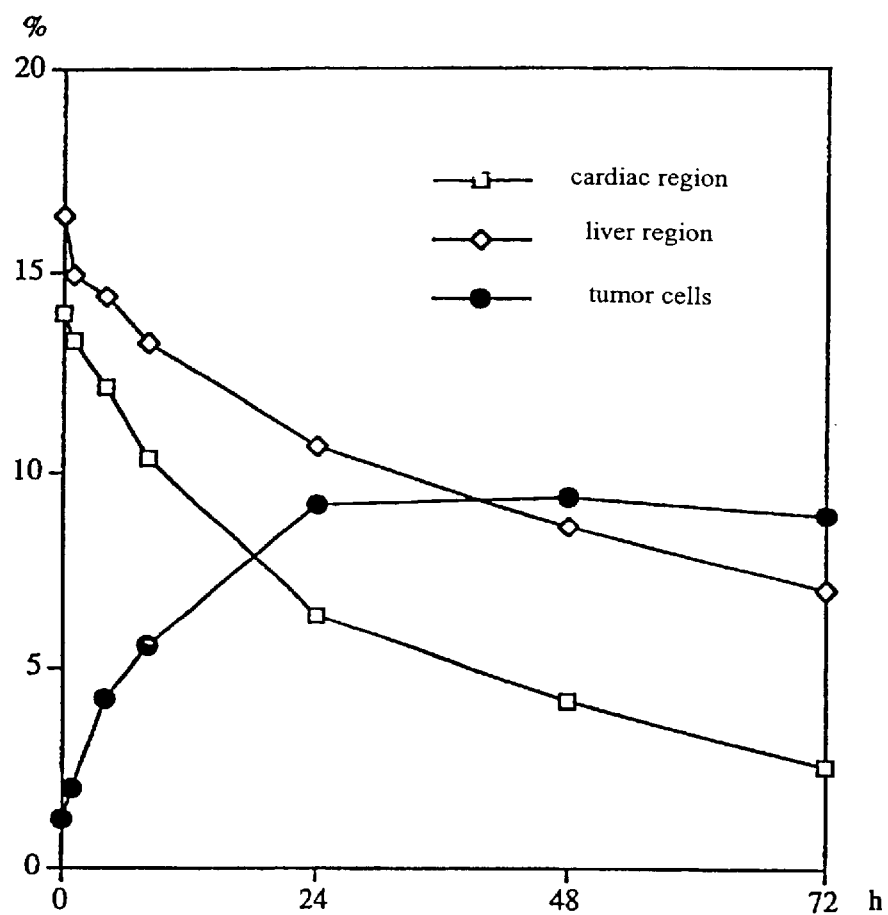
FIG. 9 shows the distribution of $^{111}$In-novantron-DTPA-HSA over the tumor, cardiac and liver regions.

In addition, the above conjugate was given to narcotized rats and the reduction of the conjugate according to the invention in the cardiac region and liver region, respectively, was measured by way of scintiscanning as usual. FIG. 9 discloses that the conjugate according to the invention concentrates in the tumor but not in the cardiac or liver region.

What is claimed is:

1. A conjugate of an active substance, a compound having a binding site for metal compounds and an albumin carrier, wherein the compound is diethylenetriaminepentaacetate, and the active substance is mitoxantrone or 1,4,5,8-tetraaminoanthraquinone.

2. The conjugate according to claim 1 wherein several active substances are present.

3. The conjugate according to claim 1 or 2 wherein several binding sites are present.

4. The conjugate according to claim 3 wherein 2 to 6 binding sites are present.

5. The conjugate according to claim 1 or 2, wherein the conjugate binds to a detectable metal compound.

6. The conjugate according to claim 5, wherein the metal compound is a detectable metal or a metal ion.

7. The conjugate according to claim 6, wherein the metal or metal ion is radioactive.

8. A process for the preparation of a conjugate according to claim 1 or 2, comprising reacting an active substance, an albumin carrier, with a compound having a binding site for metal compounds, wherein the compound is diethylenetriaminepentaacetate, and the active substance is mitoxantrone or 1,4,5,8-tetraaminoanthraquinone.

9. A composition comprising a conjugate of an active compound, carrier, and a compound having a binding site for metal compounds, wherein the carrier is selected from the group consisting of albumin and polyethylene glycol an the compound is diethylenetriaminepentaacetate, and the active substance is mitoxantrone or 1,4,5,8-tetraaminoanthraquinone.

* * * * *